United States Patent [19]

Chalmers et al.

[11] 4,328,309

[45] May 4, 1982

[54] METHOD FOR PRODUCING TRIPDIOLIDE, TRIPTOLIDE AND CELASTROL

[75] Inventors: William T. Chalmers; James P. Kutney; Phillip J. Salisbury; Kenneth L. Stuart; Phillip M. Townsley; Brian R. Worth, all of Vancouver, Canada

[73] Assignee: The United States of America as represented by the Secretary of the Department of Health & Human Services, Washington, D.C.

[21] Appl. No.: 165,336

[22] Filed: Jul. 2, 1980

[51] Int. Cl.$^3$ .................... C12N 5/00; C12N 15/00
[52] U.S. Cl. .................... 435/126; 435/127; 435/240; 435/241; 424/279; 424/317
[58] Field of Search .............. 435/126, 127, 240, 241, 435/948; 424/279, 317

[56]  References Cited

U.S. PATENT DOCUMENTS 4,005,108  1/1977  Kupchan et al. ............... 424/279 X

OTHER PUBLICATIONS

Reynolds et al., "Plant Cell Lines", *Methods in Enzymology*, vol. LVIII, Academic Press, New York, 478–486, (1979).
Bergmann, "Plating of Plant Cells", *Plant Tissue Culture and Its Bio-Technological Application*, Springer-Verlag, New York, 213, 218, (1977).
Schechter et al., *J.A.C.S.*, 64, 182–183, (1942).
Monache et al., *J.C.S. Perkin I*, 3127–3131, (1979).

*Primary Examiner*—Esther M. Kepplinger
*Attorney, Agent, or Firm*—John S. Roberts, Jr.

[57]  ABSTRACT

A process for the production of tripdiolide, triptolide and celastrol comprises the steps of:

(a) preparing a cellular inoculum from *Tripterygium wilfordii* Hook F;

(b) inoculating a nutrient growth medium with the cellular inoculum and incubating the inoculated growth medium at 20°–30° C. for up to 8 weeks to produce a cellular product;

(c) harvesting the cellular product from the inoculated growth medium; and (d) isolating tripdiolide, triptolide and celastrol from the cellular product and supernatant inoculated growth medium.

9 Claims, No Drawings

METHOD FOR PRODUCING TRIPDIOLIDE, TRIPTOLIDE AND CELASTROL

The invention described herein was made in the course of work under a grant or award from the Department of Health and Human Services.

TECHNICAL FIELD

This invention relates to a method of producing and recovering tripdiolide, triptolide and celastrol using cell cultures of the plant *Tripterygium wilfordii*.

Tripdiolide (R is OH) and triptolide (R is H), compounds of Formula I, are anti-leukemic

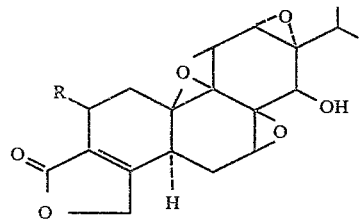

agents which have very high activity at dosage levels of micrograms/kilogram of body weight.

A quinone-methide compound, celastrol (Formula (II), has also been isolated from *T. wilfordii* Hook F and

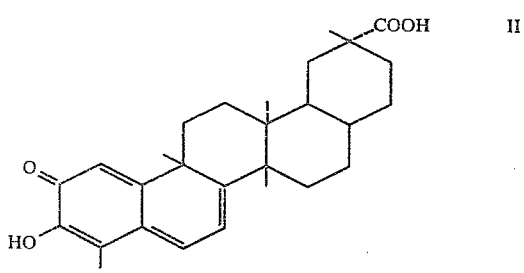

has anti-tumor activity.

BACKGROUND ART

Tripdiolide ($C_{20}H_{24}O_7$), triptolide ($C_{20}H_{24}O_6$) and triptonide ($C_{20}H_{22}O_6$) were first isolated from the roots of *T. wilfordii* Hook F by Kupchan et al, *J. Am. Chem. Soc.*, vol. 94 (1972) at 7194–7195, herein incorporated by reference. The amounts of tripdiolide and triptolide isolated from this natural source were about 0.001% by weight of the plant dry weight.

Kupchan et al, In U.S. Pat. No. 4,005,108, have further described the isolation of minute amounts of triptonide, triptolide and tripdiolide from the ground roots of *T. wilfordii* Hook F.

Celastrol or tripterine is a red pigment isolated from the roots of both *T. wilfordii* and *Celastrus scandens*, as disclosed by Schechter et al, *J. Am. Chem. Soc.*, vol. 64 (1942) at 182–183, incorporated herein be reference. Celastrol can be converted by reaction with diazomethane, in a reaction followed by column chromatography, to a methyl ester (pristimerin) m.p. 214°–217°, $C_{30}H_{40}O_4$.

Celastrol is a member of a group of triterpene-type compounds called quinone-methides. Closely related compounds, tingenone and pristimerin, have been isolated from *Maytenus chuchuhuasca* Raymond Hamet, a plant which has been used in Ecuador for skin cancer treatment (see P. Martinod, A. Paredes, F. D. Monache and G. B. Marini-Bettolo, *Phytochemistry*, Vol. 15 (1976) at 562–563.

The isolation and characterization of some related quinone-methides, including pristimerin, has been reported by Monache et al, *J. Chem. Soc. Perkin* I (1979) at 3127–3131. Some of these compounds also have antineoplastic effect.

In view of the promising anti-leukemic activity of tripdiolide and triptolide and of the anti-tumor activity of celastrol, it will be apparent that there is a need for synthetic routes producing reasonable amounts of these materials.

It is an object of this invention to provide a process for selective production, in reasonable yields, of tripdiolide, triptolide and celastrol by plant cell culture.

DISCLOSURE OF INVENTION

This invention relates to a process for obtaining tripdiolide, triptolide and celastrol, which comprises:

(a) preparing a cellular inoculum from *Tripterygium wilfordii* Hook F;

(b) inoculating a nutrient growth medium with the cellular inoculum and incubating the inoculated growth medium at 20°–30° C. for up to 8 weeks to produce a cellular product;

(c) harvesting the cellular product from the inoculated growth medium; and (d) isolating tripdiolide, triptolide and celastrol from the cellular product and supernatant inoculated growth medium.

*Tripterygium wilfordii* Hook F is a plant of the Celastraceae family, which grows in Taiwan. A domestic source of plant material is available at the Plant Introduction Garden of the Bureau of Plant Industry, at Glenn Dale, Md.

Any part of the *T. wilfordii* Hook F plant can be used to provide the explant or initial cells from which an inoculum can be prepared. However, cells from the leaves are preferred. The cellular explant is maintained on suitable plant cell culture nutrient media, the product thereof serving as inoculum for the production of tripdiolide, triptolide and celastrol. In the initial phase of inoculum production, the cells are allowed to multiply in the presence of light.

The nutrient media employed for preparing the cellular inoculum and in which multiplication of the thus-produced cells to produce a cellular product is one which will contain sources of carbon, calcium, nitrogen, magnesium, phosphorus, sulfur and potassium. Usually, and preferably, the medium will also contain vitamins. Representative of media which can be used as the basis for preparing inoculum and growing cellular products are those designated as PRL-4 and B5, compositions of which are given below.

| Medium: | mg/l of ingredient | |
|---|---|---|
| | PRL-4 | B5 |
| $NaH_2PO_4 \cdot H_2O$ | 90 | 150 |
| $Na_2HPO_4$ | 30 | |
| KCl | 300 | |
| $(NH_4)_2SO_4$ | 200 | 134 |
| $MgSO_4 \cdot 7H_2O$ | 250 | 250 |
| $KNO_3$ | 1000 | 2500 |
| $CaCl_2 \cdot 2H_2O$ | 150 | 150 |
| KI | 0.75 | 0.75 |

-continued

| Medium: | mg/l of ingredient | |
|---|---|---|
| | PRL-4 | B5 |
| Iron[a] | 28 | 28 |
| Micronutrients[b] | 1.0 ml | 1.0 ml |
| Vitamins[c] | 10.0 ml | 10.0 ml |
| Sucrose | 20.0 g | 20.0 g |
| Casein hydrolysate | 2.0 | |
| Final pH | 6.2 | 5.5 |

[a]Sequestrene 330Fe (Geigy Agric. Chem., Saw Mill River Rd., Ardsley, NY).
[b]Stock solution. Dissolved in 100 ml water: 1 g $MnSO_4 \cdot H_2O$, 300 mg $H_3BO_3$, 300 mg $ZnSO_4 \cdot 7H_2O$, 25 mg $Na_2MoO_4 \cdot 2H_2O$, 25 mg $CuSO_4$, 25 mg $CoCl_2 \cdot 6H_2O$.
[c]Stock solution. Dissolved in 100 ml $H_2O$: 10 mg nicotinic acid, 100 mg thiamine, 10 mg pyridoxine, 1 g myoinositol.

Details on other media which can be used for preparing *T. wilfordii* Hook F cultures are given in the book "Plant Tissue Culture Methods," O. L. Gamborg and L. R. Wetter, Editors, (1975), National Research Council of Canada, Prairie Regional Laboratory, Saskatoon, Saskatchewan, Canada, S7N 0W9. Of the media available, one based on PRL-4 is preferred.

Although nutrient media generally contain a source of inorganic nitrogen, such as ammonium sulfate, it is normally preferred to include in the growth medium a source of organic nitrogen. Among the sources which are preferred are casein hydrolysate. A typical casein hydrolysate can be purchased from Sheffield Chemical, Norwick, NY. This is an enzyme-(pancreatin) digested product, which has the following typical amino acid composition:

| Amino acid | % w/w protein |
|---|---|
| Alanine | 2.4 |
| Arginine | 1.4 |
| Aspartic acid | 3.7 |
| Cystine | 0.3 |
| Glutamic acid | 4.2 |
| Glycine | 1.0 |
| Histidine | 0.7 |
| Isoleucine | 2.7 |
| Leucine | 3.5 |
| Lysine | 3.7 |
| Methionine | 1.7 |
| Phenylalanine | 0.7 |
| Serine | 9.6 |
| Proline | 4.1 |
| Threonine | 2.5 |
| Tyrosine | 3.1 |
| Valine | 4.1 |

Additional analysis is as follows:

| Acid hydrolysis | w/w casein |
|---|---|
| Total nitrogen | 8.3 |
| Amino nitrogen | 6.4 |
| AN/TN ratio | 77.2 |
| Sodium chloride | 38.0 |
| Ash | 39.0 |
| Moisture | 3.5 |

Sources of carbon in the growth media include, but are not limited to, sucrose, which is included in the preferred medium. Coconut milk, which also contains various carbohydrates, is among the preferred additives for providing additional carbon in the media used in the practice of this invention.

A source of magnesium is a soluble magnesium salt, such as magnesium chloride or magnesium sulfate. Magnesium sulfate is generally preferred.

Salts of orthophosphoric acid will generally be employed as the source of phosphorus in the media used. These materials will generally be water-soluble salts, such as sodium dihydrogen phosphate and disodium hydrogen phosphate. The corresponding potassium salts can also be substituted.

Soluble inorganic sulfur compounds are used as the source of sulfur in the growth media. Typical of such salts are ammonium and magnesium sulfates.

Sources of potassium include soluble potassium salts, such as potassium chloride or potassium nitrate. Potassium nitrate is preferred.

Generally the media also will contain iodides, iron salts and other micronutrients, such as manganese salts, zinc salts, copper salts, cobalt salts, as well as sources of boron and molybdenum.

The media preferably will also contain vitamins, of which nicotinic acid, thiamine, pyridoxine and myoinositol are exemplary.

The media also should contain a soluble calcium source, such as calcium chloride.

Culturing to obtain the inoculum is essentially done in two steps, the first of which is done in the presence of light in a medium containing a first phytohormone and coconut milk to produce a callus or neoplastic growth. Phytohormones which can be used at this point include, but are not limited to, 2,4-dichlorophenoxyacetic acid, 1-naphthalene acetic acid and indole-3-acetic acid. The phytohormone of choice in this step is indole-3-acetic acid, at a level of 0.1-3 mg/l. The amount of coconut milk added to the medium may be varied from 50-150 ml/l.

It is preferred to incubate explant material to form the callus on a solid medium. Agar is representative of materials which may be used to gel the medium in amounts of up to about 1% by weight. The medium will generally have a pH of the order of 6.0-6.5.

Incubation to produce the callus is done at ambient conditions, 20°-30° C. A callus of 3-10 mm in diameter will generally be produced within about 6 weeks.

At this point, samples of callus are transferred to a liquid medium, which in addition to the base ingredients, preferably will contain casein hydrolysate, coconut milk and a second phytohormone. The phytohormone can be the same as selected for production of the callus, or may be different. However, use of 2,4-dichlorophenoxyacetic acid at a level of 1-3 mg/l is preferred.

A suspension of cells and cellular aggregates obtained from the callus and transferred to the liquid medium are shaken on gyratory shakers (150 rpm) in the dark for several weeks, generally 6-8 weeks. The cellular inoculum thus obtained is used to produce cellular product, from which the active diterpenoid materials can be isolated.

Incubation of the cellular inoculum is done in a liquid nutrient growth medium, generally as above, but which contains on the order of 5-10 ml/l of coconut milk. The pH of this medium is generally about 5.9. The liquid cultures are shaken, as above, in subdued light for several weeks, generally 6-8 weeks. It is important that the pH of the cellular suspension be monitored and maintained below 7 during the growth period, conveniently using a mineral acid; e.g., HCl, $H_2SO_4$ or $H_3PO_4$.

It is acceptable, and generally is preferred, to transfer cellular material to a fresh batch of growth media about half way into the incubation period.

At the end of the incubation period, cellular product is removed from the supernatant nutrient growth medium, conveniently by filtration. The thus-harvested cellular product is crushed and extracted with ethyl acetate. The supernatant medium is also extracted with ethyl acetate and the combined ethyl acetate extracts are evaporated to dryness to produce a crude mixture of tripdiolide, triptolide and celastrol.

A preferred procedure for isolating the individual components of the crude product is by column chromatography on silica, using a gradient going from benzene to ethyl acetate.

It is proposed that, in the case of Tripterygium cultures, cytophysiological conditions favorable for the production of metabolites requires a degree of cellular differentiation. Generally, the percentage of differentiated cells is proportional to the amount of accumulated metabolites. It should be noted that cellular differentiation and cell division are mutually exclusive, so that cellular differentiation exclusively will prevent an increase in the number of cells.

In the *T. wilfordii* cultures employed in the practice of this invention, cellular differentiation is induced by decreasing limiting growth factors, such as nitrogen, carbohydrates and growth hormones. Accordingly, after a time, the limiting growth factor or factors will be exhausted and cellular differentiation will be succeeded by increase in cell division.

It has been observed, in cultures of *T. wilfordii* Hook F, that product accumulation increases as the percentage of differentiated cells increases. Also, root formation has been noted in some cases.

It will be understood that advantages of the process of the invention include not only higher yields of triptolide and related materials than obtainable from plant extracts but also that the proportions of triptolide, etc. are different than obtainable from the plant extracts.

It will be understood that, although the biosynthetic potential of in vitro cell cultures can be utilized for the synthesis and accumulation of species-specific metabolites, the rate of production and the amount of product accumulation is, at least partially, determined by the genotype of a specific cell line. Accordingly, it is contemplated that selection of cell lines with superior metabolite production tendencies is feasible. Techniques for obtaining superior cell lines would include induction of mutations and selection of highly active mutant cell lines for their capacity to accumulate high levels of tripdiolide, triptolide and celastrol.

BEST MODE FOR CARRYING OUT THE INVENTION

In a most preferred embodiment, the process will be carried out as above, wherein the cellular inoculum is prepared from the leaves of *T. wilfordii* Hook F, wherein preparation of the cellular inoculum and incubation of the cellular inoculum to produce cellular product is done in media containing coconut milk, vitamins and sources of carbon, nitrogen, magnesium, calcium, phosphorus, sulfur and potassium; wherein preparation of the cellular inoculum is done in the presence of light in a medium containing indole-3-acetic acid to produce a callus and material from the callus is further incubated in the dark in a medium containing casein hydrolysate and 2,4-dichlorophenoxyacetic acid and wherein incubation of the cellular inoculum in the nutrient growth medium to produce cellular product is done under subdued light and the pH of the nutrient growth medium is maintained below 7.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever. In the following Examples, the temperatures are set forth uncorrected in degrees Celsius. Unless otherwise indicated, all parts and percentages are by weight.

EXAMPLE 1

Preparation of Cellular Inoculum

Nutrient medium was prepared using the PRL-4 formulation, to which was added 2 mg per liter of indole-3-acetic acid and 100 ml of coconut milk per liter and 0.6% by weight of agar. The pH of the medium was 6.2 prior to sterilization by autoclaving.

Leave or stem material from *Tripterygium wilfordii* Hook F was sterilized at the surfaces thereof and placed on the agar plates. The inoculated agar plates were incubated at ambient conditions (20°–30° C. and normal light) for about six weeks. A resulting callus or neoplastic growth 3–10 mm in diameter was obtained.

The callus was transferred to 100 ml of fresh PRL-4 liquid medium modified with 2 g/l of casein hydrolysate, 10 ml/l of coconut milk and 2 mg/l of 2,4-dichlorophenoxyacetic acid. The resulting suspension of cells and cellular aggregates was shaken on a gyratory shaker (150 rpm) in the dark for 6–8 weeks. The product obtained was used as inoculum for 250 ml portions of the liquid PRL-4 medium.

EXAMPLE 2

Incubation to produce tripdiolide, triptolide and celastrol

Portions of PRL-4 medium containing 6 ml/l of coconut milk and having a pH of 5.9 were shaken in 2 liter flasks with cellular inoculum obtained as above. The cultures were shaken in subdued light for 6–8 weeks under ambient conditions. The pH of the medium was monitored continuously. The pH was adjusted as necessary, so as to be maintained below pH 7. At the end of the incubation period, cellular material was removed from the medium by filtration. The weight of cellular material harvested from 28 l of medium was 6 kg.

EXAMPLE 3

Isolation of tripdiolide triptolide and celastrol

The mother liquor remaining from filtration of the cellular products (28 l) was extracted with two 10 l portions of ethyl acetate. The combined cellular product (6 kg) were crushed and extracted with two 3 l portions of ethyl acetate at room temperature and then with two 3 l portions of 100% ethanol. Following removal of ethanol by evaporation under vacuum, the residue was taken up in 500 ml water and extracted with two 500 ml portions of ethyl acetate. The combined ethyl acetate extracts were evaporated to dryness on a rotary evaporator. The residue of dark brown material weighed 17 g.

The crude product was separated by column chromatography on 700 g silica packed in benzene. A total of twenty 500 ml fractions of eluate were collected, the eluting solvents being of the following compositions:

| Fractions | Eluting Solvent |
|---|---|
| 1-2 | Benzene |
| 3-5 | 5% Ethyl Acetate - 95% Benzene |
| 6-8 | 10% Ethyl Acetate - 90% Benzene |
| 9-10 | 15% Ethyl Acetate - 85% Benzene |
| 11-15 | 20% Ethyl Acetate - 80% Benzene |
| 16-17 | 30% Ethyl Acetate - 70% Benzene |
| 18-20 | 100% Ethyl Acetate |

TLC analysis indicated that tripdiolide was isolated in fractions 19 and 20, triptolide in fractions 6-7 and celastrol in fractions 8-14.

EXAMPLE 4

Purification of tripdiolide

Crude tripdiolide (1.2 g) from fractions 19 and 20 were purified on a column packed with 150 g silica in diethyl ether. The following eluting solvents, in 250 ml portions, were used:

| Fractions | Eluting Solvent |
|---|---|
| 1-3 | Diethyl ether |
| 4-6 | 1% Ethanol - 99% Diethyl ether |
| 7-8 | 2% Ethanol - 98% Diethyl ether |
| 9-10 | 3% Ethanol - 97% Diethyl ether |
| 11-13 | 5% Ethanol - 95% Diethyl ether |
| 14-15 | 10% Ethanol - 90% Diethyl ether |

Tripdiolide was isolated from fractions 11-15. Further purification was accomplished using Merck 2 mm and 0.25 mm silica plates in ethyl acetate and 2% ethanol-diethyl ether. The product was identified by TLC comparative studies, mass spectral analysis and PMR analysis (270 MHz), compared with an authentic sample of tripdiolide. The yield was 0.003% of the dry cell weight.

EXAMPLE 5

Identification of triptolide

The presence of triptolide in fractions 6-7 of the product of Example 3 was confirmed by TLC analysis and comparison with a known specimen. In vitro action against cells derived from human carcinoma of the nasal pharynx (KB) was demonstrated by standard NCI protocols.

EXAMPLE 6

Isolation of celastrol

Celastrol was isolated from fractions 8-14, obtained in Example 3, by preparative TLC on 2 mm silica plates developed in methanol-chloroform (1:20). The identity of the product was confirmed by spectral comparison with an authentic sample of celastrol. Evaluation for in vitro activity against KB cells gave a value of $ED_{50} = 5 \times 10^{-1}$. The yield of celastrol was about 0.1% of the dry cell weight.

The preceding examples can be repeated with similar success by substituting the generically or specifically described reactants and/or operating conditions of the invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

We claim:

1. A process for obtaining tripdiolide, triptolide and celastrol comprising the steps of:
    (a) preparing a cellular inoculum from *Tripteryguim wilfordii* Hook F;
    (b) inoculating a nutrient growth medium with the cellular inoculum and incubating the inoculated growth medium at 20°-30° C. for up to 8 weeks to produce a cellular product at a pH below 7;
    (c) harvesting the cellular product from the inoculated growth medium; and
    (d) isolating tripdiolide, triptolide and celastrol from the cellular product and supernatant inoculated growth medium.

2. The process of claim 1, wherein the cellular inoculum is prepared from the leaves of *T. wilfordii* Hook F.

3. The process of claim 1, wherein preparation of the cellular inoculum and incubation of the cellular inoculum to produce cellular product is done in media containing sources of carbon, nitrogen, magnesium, calcium, phosphorus, sulfur and potassium;

4. The process of claim 3, wherein the media contain vitamins.

5. The process of claim 1, wherein preparation of the cellular inoculum is done in the presence of light in a medium containing a first phytohormone and coconut milk to produce a callus and wherein material from the callus is further incubated in the dark in a medium containing casein hydrolysate, coconut milk and a second phytohormone.

6. The process of claim 5, wherein the first phytohormone is indole-3-acetic acid and the second phytohormone is 2,4-dichlorophenoxyacetic acid.

7. The process of claim 1, wherein incubation of the cellular inoculum in the nutrient growth medium to produce cellular product is done under subdued light and the pH of the medium is maintained below 7.

8. The process of claim 7, wherein the nutrient growth medium contains coconut milk.

9. The process of claim 1, wherein the cellular inoculum is prepared from the leaves of *T. wilfordii* Hook F; wherein preparation of the cellular inoculum and incubation of the cellular inoculum to produce cellular product is done in media containing coconut milk, vitamins and sources of carbon, nitrogen, magnesium, calcium, phosphorus, sulfur and potassium; wherein preparation of the cellular inoculum is done in the presence of light in a medium containing indole-3-acetic acid to produce a callus and material from the callus is further incubated in the dark in a medium containing casein hydrolysate and 2,4-dichlorophenoxyacetic acid and wherein incubation of the cellular inoculum in the nutrient growth medium to produce cellular product is done under subdued light and the pH of the nutrient growth medium is maintained below 7.

* * * * *